United States Patent [19]

Berger et al.

[11] Patent Number: 4,967,095
[45] Date of Patent: Oct. 30, 1990

[54] METHOD AND APPARATUS FOR DETECTING AND SIZING PARTICLES ON SURFACES

[75] Inventors: Josef Berger, Los Altos; Armand P. Neukermans; John L. Vaught, both of Palo Alto, all of Calif.

[73] Assignee: Tencor Instruments, Mountain View, Calif.

[21] Appl. No.: 411,910

[22] Filed: Sep. 25, 1989

Related U.S. Application Data

[63] Continuation-in-part of Ser. No. 373,026, Jun. 28, 1989, abandoned.

[51] Int. Cl.$^5$ ............................................. G01N 21/88
[52] U.S. Cl. ................. 250/572; 250/222.2; 356/37
[58] Field of Search ............... 250/222.2, 223 R, 562, 250/563, 571, 572, 559; 356/37, 237, 429, 430, 431

[56] References Cited

U.S. PATENT DOCUMENTS

| | | |
|---|---|---|
| 2,128,228 | 8/1938 | Betz et al. |
| 2,584,988 | 2/1952 | Dember. |
| 3,131,557 | 5/1964 | Hoy. |
| 3,580,066 | 5/1971 | Pliskin et al. |
| 3,618,374 | 11/1971 | Miller. |
| 4,215,562 | 8/1980 | Gavrilin. |
| 4,314,474 | 2/1982 | Dermarderosian. |
| 4,449,816 | 5/1984 | Kohsaka et al. ............... 356/37 |
| 4,601,576 | 7/1986 | Galbraith ....................... 356/237 |
| 4,740,708 | 4/1988 | Batchelder ...................... 250/572 |
| 4,792,199 | 12/1988 | Borden ............................ 356/37 |

Primary Examiner—Edward P. Westin
Attorney, Agent, or Firm—Thomas Schneck

[57] ABSTRACT

A method and apparatus for detecting and classifying particles on a surface in which condensation is used to enlarge particles. An apparatus of the present invention includes a heatable wick disposed over a test surface and in fluid communication with a source of volatile liquid. A zone of vapor supersaturation is thus created in which condensation on particles on the surface can occur. A light beam directed onto the surface scans the surface. Droplets are detected by means of light scattered from the droplets. In an alternate embodiment a stream of carrier gas may be provided around the wick or bubbled through a jar of volatile liquid to direct a vapor toward the test surface. In another embodiment, multiple wicks communicate with different sources of volatile liquids. In a method of the invention, mulitple scans are made with either different levels of vapor supersaturation or different vapor compositions. Comparing particles in each scan allows one to classify particles into different size ranges or chemical type.

30 Claims, 5 Drawing Sheets

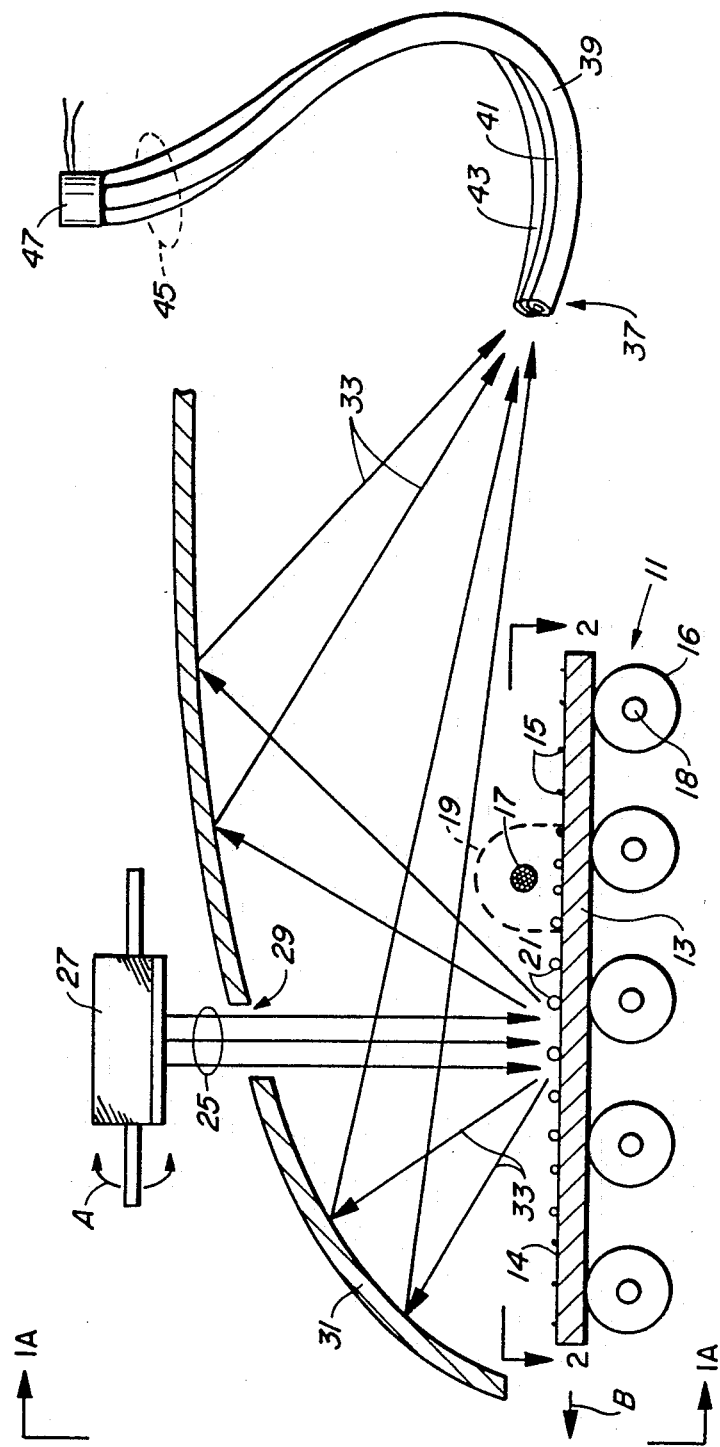
FIG._1.

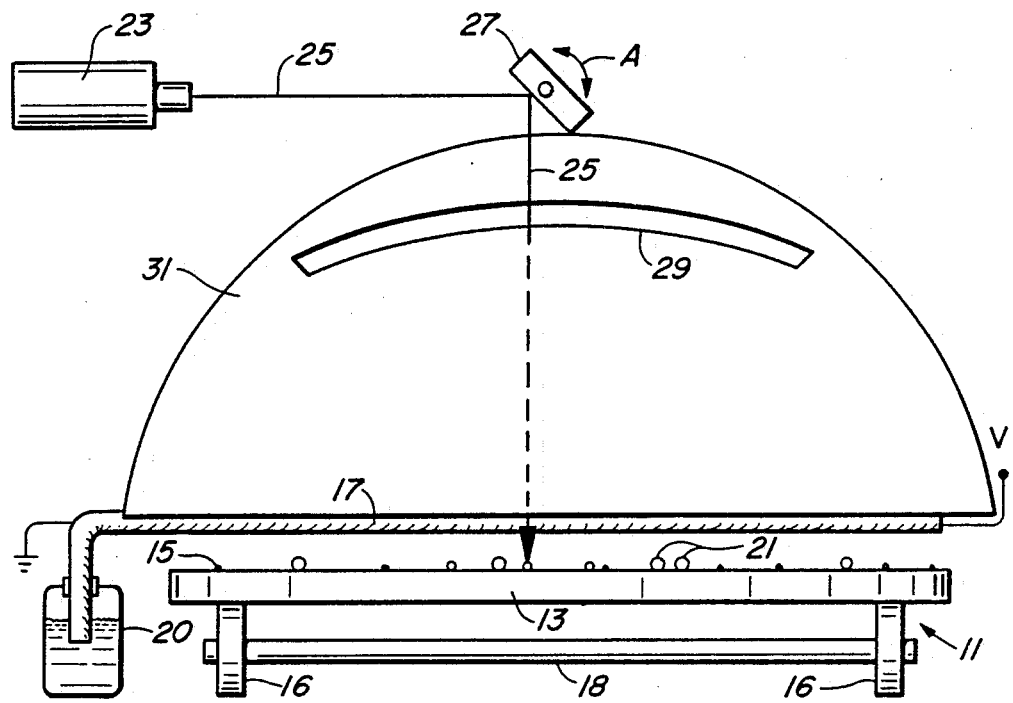
FIG._1A.
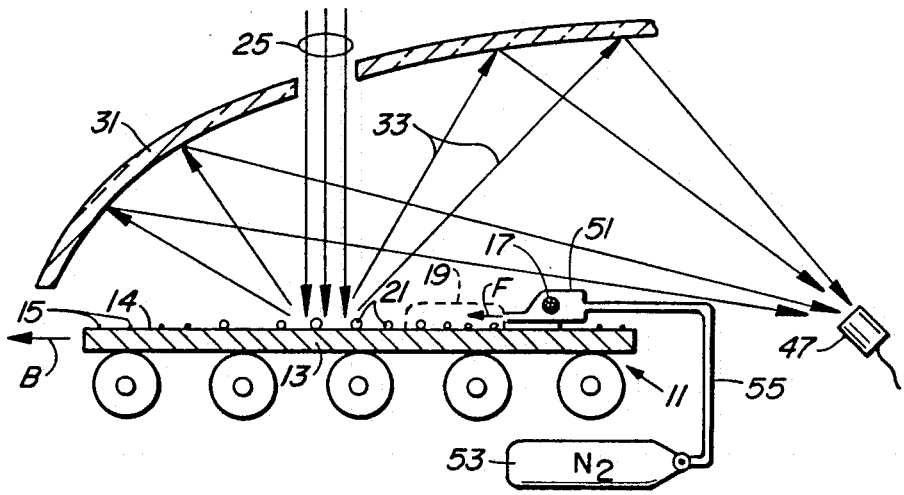
FIG._3.

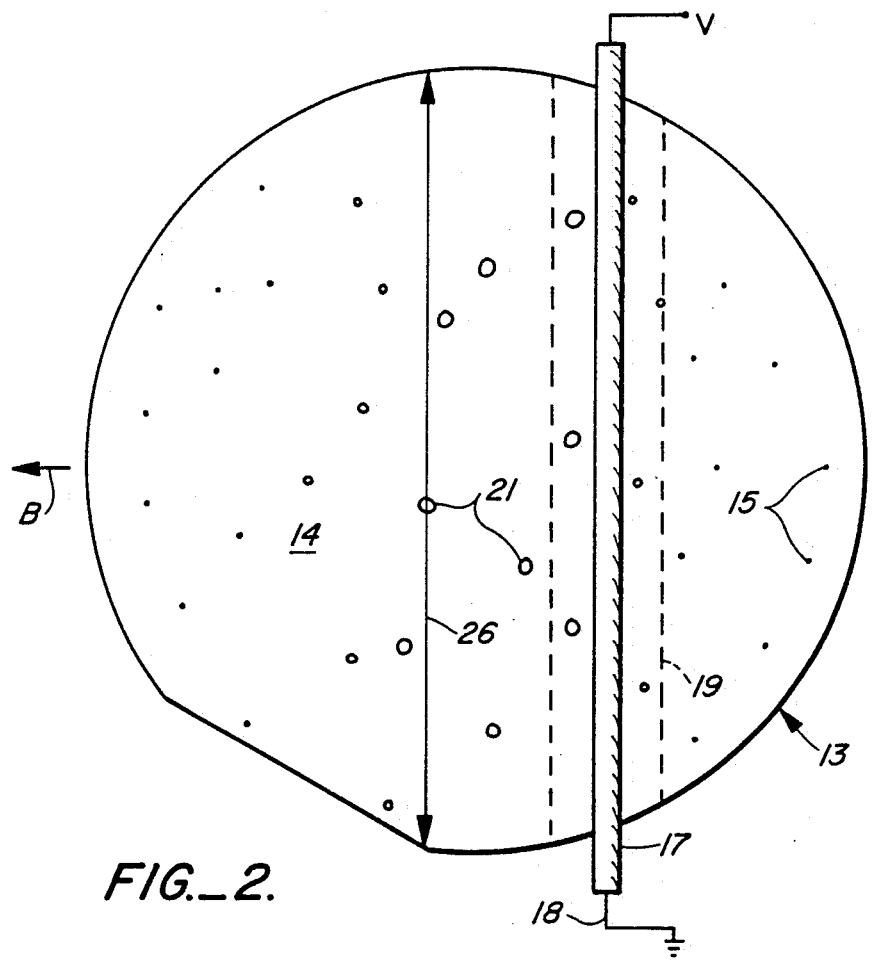
FIG._2.
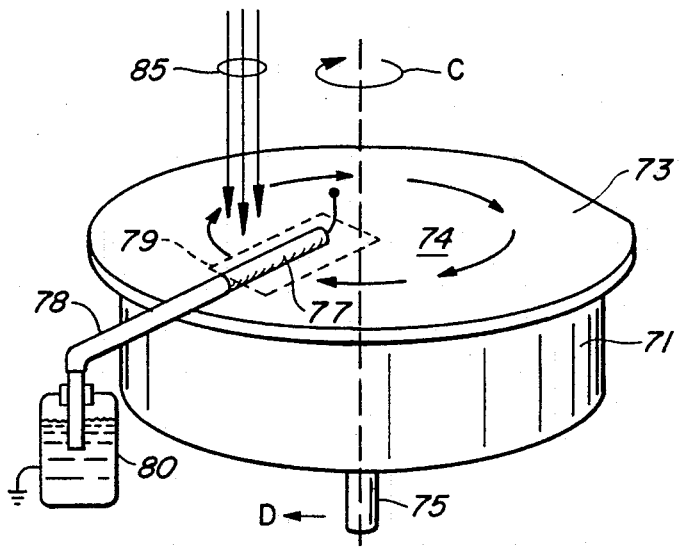
FIG._8.

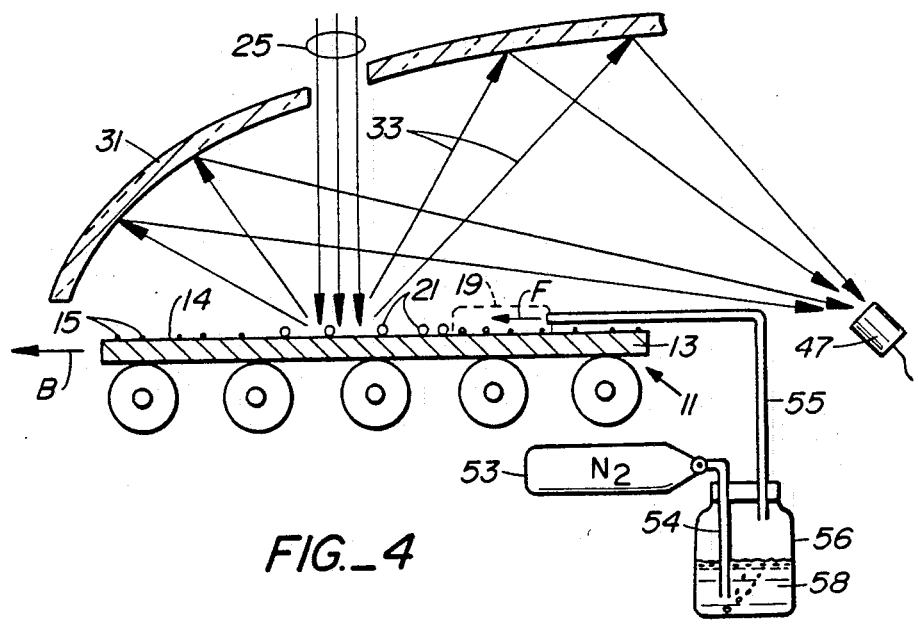
FIG._4
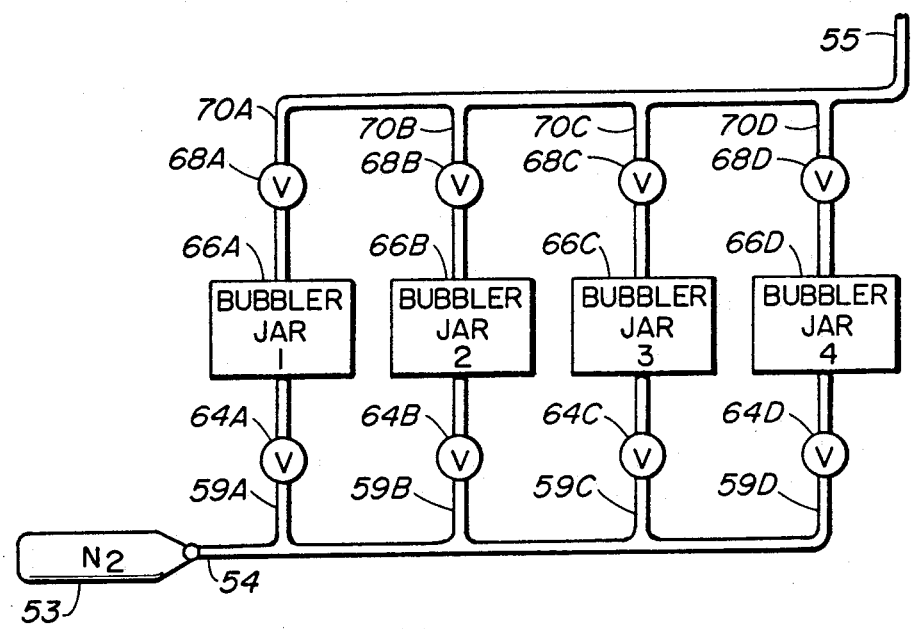
FIG._7

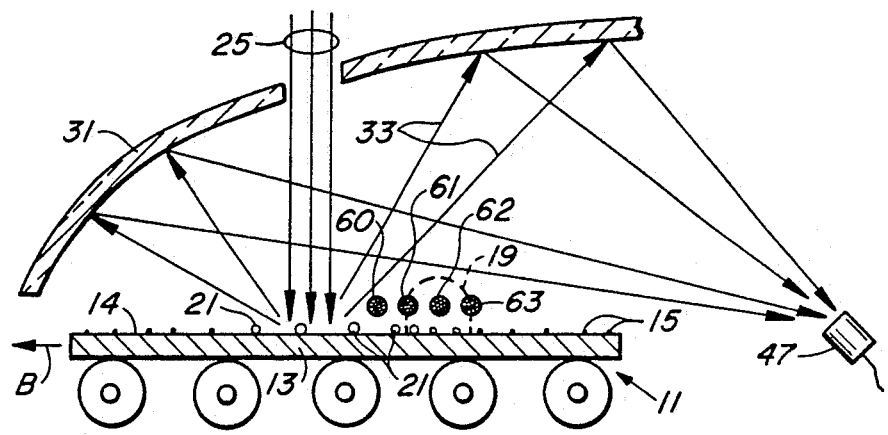
FIG._5.
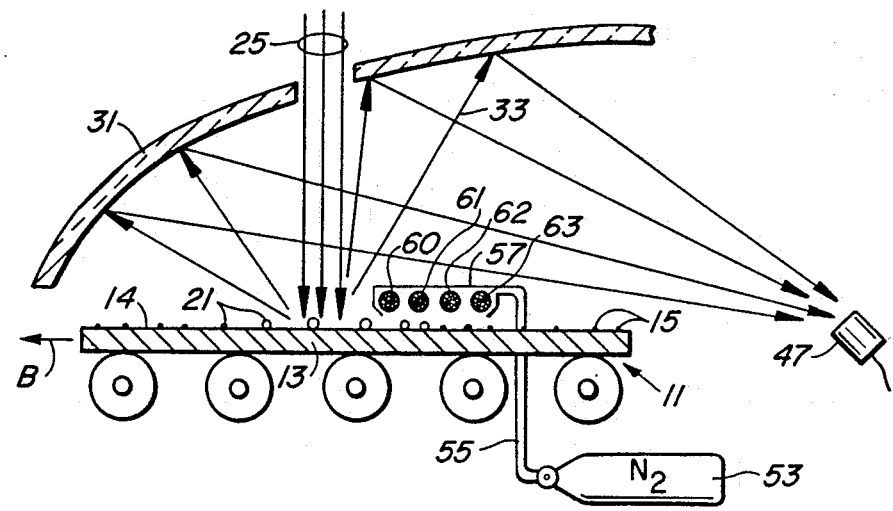
FIG._6.

METHOD AND APPARATUS FOR DETECTING AND SIZING PARTICLES ON SURFACES

CROSS REFERENCE TO RELATED APPLICATION

This is a continuation-in-part of Ser. No. 373,026, filed June 28, 1989, now abandoned.

TECHNICAL FIELD

The present invention relates to optical detection, location and size measurement of very small particles on surfaces, such as wafer substrates, and in particular to methods and apparatus which detect light reflected or scattered from a test surface on which vapor has condensed.

BACKGROUND ART

Contaminating particles are a major source of yield loss in the semiconductor industry. Accordingly, instruments have long been used to detect, locate and size particles on semiconductor wafers. Presently, the practical detection limit of particles on bare silicon wafers is about 0.1 to 0.2 micrometers. Because the amount of scattered light from a particle is proportional to $d^6$, where d is the particle diameter, a reduction in particle size by a factor of 2 results in a 64-fold decrease in scattered light. Because a reasonable overall detection rate of about one to three wafers per minute is desired, and the number of photons scattered from a moving laser beam gets to be small around 0.1 micrometers, detection runs into a practical limitation around this size.

However, even though particles smaller than 0.1 micrometers cannot be reliably detected by currently available instrumentation operating at an inspection rate of one to three wafers per minute, does not mean that they are necessarily harmless. Such very small particles, although substantially smaller than the present critical line widths, are still considered very detrimental on very thin films. Here the important parameter is particle size with respect to film thickness, rather than line width. These particles may cause pin holes in a thin film and reduced dielectric strength, thereby causing premature breakdown.

In the semiconductor industry, condensation nucleus counters are used to detect very small particles suspended in the air of a clean room. This type of detector works on the principle that particles in free space act as nucleation centers for supersaturated vapor and can thus be artificially enlarged by condensing liquid onto the particles so as to form droplets that can be detected. An airstream is saturated with, for example, alcohol vapor, then enters a condensing region, where droplets form around any particles suspended in the airstream and grow in size until they reach a detection chamber. There the particles are detected and counted by virtue of the light scattered from the droplets. Typically, condensation nucleus counters can detect particles suspended in air down to a size on the order of 0.01 micrometers. It is, however, difficult to control the growth process so as to maintain adequate size discrimination between the original particles.

In U.S. Pat. No. 4,314,474, Dermarderosian describes a method in which an inert fluorocarbon vapor is condensed on a test surface in order to detect cracks, fissures and other such faults on the surface. Liquid fluorocarbon contained in a flask is heated to a gentle boil while an inert gas, such as air or nitrogen, is bubbled through the liquid. A mild flow of vapor is carried from the flask to the test surface by a vapor tube, the free end of which is held ½ inch to 1 inch (approx. 2 cm) away from the test surface. The fluorocarbon has a surface tension sufficiently low that as it condenses it wets the surface, forming a layer of uniform thickness. Detection is visual and may be made with the aid of a microscope and relies on the fact that faulted regions absorb comparatively more of the incident light than unfaulted regions. Defects on the order of one micrometer in size are visible.

In U.S. Pat. No. 3,580,066, Pliskin describes a method of determining the completeness of oxide etching of via holes in a silicon member surface, in which the silicon member is cooled while a stream of moist gas is directed onto its surface. The stream of moist gas is produced by bubbling dry nitrogen through deionized water. Condensation in the holes is in the form of a thin film over residual oxide but beads into droplets over bare silicon.

It is an object of the present invention to provide an apparatus for detecting particles and surface features smaller than 0.1 micrometers on a test surface.

It is another object of the invention to provide a method for estimating the sizes of detected particles, as well as characterize the types of particles present on the test surface.

DISCLOSURE OF THE INVENTION

The above objects have been met with a particle detection apparatus combining a heated wick or other means for providing a local region of controlled supersaturation over a surface to be tested and a laser scanner or other means for directing a beam toward the surface adjacent to the region of supersaturation to detect condensed droplets. The objects are also met with a method using repeated scanning of a surface with different supersaturation levels or different vapor compositions in order to classify the particles, by relative size or some other characteristic, according to the particular scan or scans in which droplets are detected.

The particle detector of the present invention includes a support for an object with a surface to be tested such as a semiconductor wafer. The detector also includes a source of vaporizable liquid material, such as alcohol, and a wick in fluid communication with the liquid source so as to draw the liquid from the source into the wick. Heating the wick vaporizes the liquid material, and since the wick is disposed over a portion of the surface, it provides a local zone of vapor over that surface portion. In one embodiment, a source of a carrier gas, such as nitrogen, and a manifold communicating with the carrier gas source may be provided for directing a vapor stream toward a portion of the surface. Preferably, the velocities of the vapor stream and wafer are colinear and equal so that there is no relative motion and therefore no turbulence. With or without the carrier gas, since the surface is cooler than the vapor condensation temperature or "dew point", the local vapor zone is supersaturated and droplets of liquid condense around any particles on that portion of the test surface. A scanning laser or other directed beam source provides a beam directed toward the surface adjacent to the zone of vapor supersaturation. A track or other means may be provided for moving the object on its support relative to the supersaturation zone and adjacent beam so that condensed droplets on the object's surface move into the beam path. A detector is positioned to receive the beam light scattered by the droplets, whereby particles are detected by means of the condensed droplets. In another embodiment, plural sources of vaporizable material of different compositions and plural heatable wicks may be provided for selecting a particular vapor to be used.

The method of the present invention takes advantage of the controlled supersaturation of the above described detector to detect and classify the particles on a test surface. A first supersaturated vapor is provided over the test surface and the surface is scanned for droplets. This is repeated a number of times with other supersaturated vapors and the detections from different scans are compared so as to classify the particles according to the particular scan or scans in which the particles are detected. For example, the vapors in the various scans may be distinguished by varying supersaturation levels, with detectable droplets condensing on particles of at least a certain minimum size for any given supersaturation level. The particles can then be classified into relative size ranges corresponding to the supersaturation level needed for their detection. Alternatively, vapors may be distinguished by their composition, polar materials tending to condense around ionic salt particles, non-polar materials tending to condense around non-ionic material, photoresist solvents tending to condense around photoresist residue, etc.

BRIEF DESCRIPTION OF THE DRAWINGS

FIG. 1 is a side sectional view of a particle detector of the present invention.

FIG. 1A is a front sectional view taken along the line 1A–1A in FIG. 1.

FIG. 2 is a top plan of a wafer with particles and a wick of the particle detector taken along the line 2—2 in FIG. 1.

FIG. 3 is a side sectional view of a scanning portion of a second particle detector embodiment of the present invention.

FIG. 4 is a side sectional view of a scanning portion of an alternate particle detector embodiment for carrying out the method of the present invention.

FIG. 5 is a side sectional view of a scanning portion of a third particle detector embodiment of the present invention.

FIG. 6 is a side sectional view of a scanning portion of a fourth particle detector embodiment of the present invention.

FIG. 7 is a schematic side view of a multiple bubbler jar configuration for optional replacement of the single jar configuration in FIG. 4.

FIG. 8 is a perspective view of a wafer on a rotatable support and a second wick in accord with a fifth particle detector embodiment of the present invention.

BEST MODE FOR CARRYING OUT THE INVENTION

With reference to FIGS. 1, 1A and 2, a particle detector includes a support 11 for an object 13, such as a semiconductor wafer, having a surface 14 to be tested for the presence of particles 15. Here, the support 11 is represented as a plurality of wheels or rollers 16 which freely turn or are driven about axles 18. However, the particular form of support 11 for test object 13 is not critical to the present invention, and, accordingly, other types of supports could be used. The test object or wafer 13 is movable in a direction indicated by arrow B and means are generally provided for moving the object uniformly in that direction. For example, in the form of support seen in FIG. 1, some or all of the wheels 16 may be rotatably driven on a track by a motor. Again, the particular form of drive used is not critical.

The particle detector also includes a wick 17 which is positioned closely above the surface 14 of wafer 13. Typically, wick 17 is a long clean metallic wick made up of fine metal filaments loosely twisted or woven together. Such a wick can be heated by passing an electric current through it. Wicks can also be made of a metallic core with nonconductive fibers woven or twisted around the core, of a capillary tube slotted radially along its length or of a composite of metallic and nonmetallic threads as long as an electrically conductive path exists along the wick's length to provide heating. Wick 17 is in fluid communication with a source 20 of a vaporizable liquid, such as alcohol. The liquid is drawn into the wick 17 from source 20, and since wick 17 is heated by an electric current, the liquid vaporizes. This creates a local zone 19 of vapor around the wick 17 over the surface 14. The surface 14 is cooler than or is made to be cooler than the vapor condensation temperature or "dew point" so that zone 19 is supersaturated. As a result, droplets 21 condense on the surface 14 as the object 13 passes beneath wick 17. Condensation occurs only on that portion of the surface 14 which is within the local zone 19 of supersaturation. Moving the wafer 13 in the direction of arrow B brings different portions of the surface 14 into the zone 19 and also brings the condensed droplets into the path of a scanning beam 25.

A laser or other beam source 23 produces a laser light beam 25 directed at a scanning mirror 27. Mirror 27 oscillates in a direction indicated by arrows A so that the resulting scan path 26 of beam 25 on surface 14, seen in FIG. 2, is in a direction which is substantially perpendicular to the direction B of wafer movement. Scan path 26 is adjacent to the zone 19 of vapor supersaturation on the side such that just condensed droplets 21 move into the beam path 26 when wafer 13 moves.

A detector 47 is positioned to receive light 33 scattered by the droplets. A light collector is used in combination with the detector 47 in order to enhance particle detection. Many different light collector-detector combinations could be used. One preferred embodiment, shown in FIG. 1, includes an ellipsoidal shell 31 having a reflective inside surface. Shell 31 has a first focal line coinciding with the scan path 26 on the surface 14 and a second focal line coinciding with a line of input apertures 37 for a plurality of fiberoptic waveguides 39, 41, 43, etc. A slot 29 is provided in shell 29 for the scanning laser beam 25. The light collector also includes a second stage which, preferably, is a fiber optic line-to-point collector. This type of second stage comprises a plurality of fiber optic waveguides 39, 41, 43, etc. having an input end with apertures 37 arranged in a line coinciding with the second focal line of a shell 31. The waveguides 39, 41, 43, etc. are brought together at an output end to form a bundle 45. Detector 47, such as a photomultiplier tube, is optically coupled to the output end of bundle 45 to receive the light 33 transmitted through the waveguides 39, 31, 43, etc. While this form of collector-detector combination is preferred, other detection apparatus may be used to detect scattered light 33. For example, embodiments described in U.S. Pat. No. 4,601,576, assigned to the assignee of the present invention, may be used.

With reference to FIG. 3, an alternate embodiment of the present invention has, like the first embodiment in FIGS. 1 and 1A, a support 11 for an object 13 with a surface 14 to be tested for the presence of particles 15. It also has a wick 17 in fluid communication with a source of vaporizable liquid material, and which is capable of being heated so as to vaporize the liquid drawn from the source into the wick to thereby provide a local zone of vapor supersaturation over a portion of the surface. The detector also includes a laser scanner providing a beam 25 scanning the surface 14 in a direction approximately perpendicular to the direction B of motion of the test object 13, and a detector 47 positioned to receive light 33 scattered from droplets 21 condensed around particles 15 via a light collector 31.

Unlike the first embodiment, the alternate embodiment in FIG. 3 also includes a source 53 of a carrier gas and a manifold 51, which communicates with source 53 via a tube 55. The carrier gas may be nitrogen, air, or some other essentially inert gas capable of holding vapor from wick 17, and may be heated. The source 53 can be a pressurized container and valve, as shown, or a pump, either of which provides a stream of gas to manifold 51. Manifold 51 substantially surrounds the wick 17 and 11 provided with a side opening so that the stream of carrier gas, indicated by arrow F, containing the vaporized material from the wick is directed over the surface 14. Preferably, the velocity of the vapor stream F is colinear and equal to the velocity of wafer motion, indicated by arrow B. Thus, there would be no relative motion between the vapor stream and the wafer, and hence no turbulence. In this manner, a zone 19 of vapor supersaturation forms adjacent to a portion of the cooler surface 14. The wick-manifold combination should be positioned close to the surface 14, spatially removed from the neighborhood of beam 25, so that it does not interfere with the collection of scattered light 33.

The level of supersaturation, and thereby the size of the droplets 21 which are formed, can be controlled in one or more ways. By adjusting the amount of current which flows through wick 17, the heating of wick 17 can be controlled. Varying the heating of wick 17 varies the rate at which volatile liquid material drawn from source 20 vaporizes. Up to a point, hotter wicks generally result in greater supersaturation than cooler wicks. The amount of vaporization is limited by the rate at which volatile liquid can be drawn into the wick. Alternatively, vaporization from the wick can be controlled by varying the temperature of the carrier gas, as by heating the gas as it passes through tube 55. Supersaturation can also be controlled in the embodiment of FIG. 3 by varying the flow rate of the carrier gas stream past wick 17, thereby varying the concentration of vapor in the gas stream. Faster streams result in less supersaturation than slower streams. However, if this preferred embodiment of equal stream and wafer velocities is to be used, it should be realized that this latter approach is limited by a maximum wafer velocity for accurate wafer scanning. Supersaturation can also be varied to some extent by controlling the temperature of the test object. For example, a test wafer can be cooled in a controlled manner thermoelectrically or by using a fluid cooled chuck for support 11. Cooler surfaces 14 result in greater supersaturation and more condensation than room temperature surfaces.

A method of estimating the sizes of particles on a test surface relies on the ability of the above described particle detectors to vary the supersaturation. By changing the supersaturation the size of the droplets formed may be controlled. Because the particles are on a surface, their location is generally fixed and position information of detected particles can be stored for analysis. This information can be used, for example, to classify particles by relative size, eliminating a particle from a particular count at a given supersaturation level. Suppose, for example, that a 0.1 micrometer particle passes under the condensation source into the zone of supersaturation. It is likely to produce observable scattering at a low supersaturation level. Hence, a first scan is made using low supersaturation and these particles are detected, located and counted. A second scan is then made with increased supersaturation, and particles are again located and counted. This second scan will again detect particles from the first scan and will also detect smaller particles due to the greater supersaturation level forming larger droplets. Those particles observed in the first scan are eliminated from the count of the second scan. This is possible because positions are known. Repeating these steps for ever-increasing supersaturation, it is possible to trace out the particle distribution and location over the test surface.

Accordingly, a method of detecting and classifying particles on a surface comprises providing a first supersaturated vapor over a test surface, whereby droplets condense on a first set of particles on the surface, and scanning the surface so as to detect those droplets. These steps are repeated a predetermined number of times, typically not more than four or five times due to time constraints, with other supersaturated vapors, whereby droplets condense on other sets of particles on the surface and are subsequently detected. Typically, the droplets evaporate on their own after each scan, although this can be enhanced by heating the test surface or the gas environment above it. Droplet detections from the several scans are compared and the particles on the surface are classified according to which scan or scans their corresponding droplets are detected.

In the example described above, the supersaturated vapors for the several scans are distinguished by the supersaturation level and detectable droplets condense on particles of at least a particular minimum size depending on that level. Thus particles are classified into a plurality of relative size ranges corresponding to the particular supersaturation level needed for detecting condensed droplets on those particles. Comparing droplets from the several scans preferably includes locating and storing the position of detected droplets in each scan, then matching any common positions from the plurality of scans. Detections in different scans at a matching position are designated as corresponding to the same particle. An alternative, but less accurate method, simply counts the number of particles detected in each scan and using ordinary subtraction to obtain the number of particles in each class. This alternative gives a rough estimate of particles in each size range but does not locate particle positions.

The above described sizing method is preferably carried out using the apparatus shown in FIGS. 1–3, in which a wick provides the local zone of vapor supersaturation at various supersaturation levels. However, other apparatus that provide a local zone of vapor supersaturation over a portion of the test surface and that can be controlled to vary the supersaturation level could also be used. For example, in FIG. 4, a particle detection apparatus is shown which is nearly identical to that shown in FIG. 3, except that instead of a wick and manifold, a bubbler jar 56 is used. A gas source 53 communicates with bubbler jar 56 via a tubing 54 which extends down into vaporizable liquid material 58 in jar 56. Gas from source 53 bubbles through liquid 58 and becomes saturated in the process. The now vapor laden gas exits jar 56 through tube 55 which terminates above wafer 13. A stream of the vapor-laden gas is thus directed over wafer surface 14, as indicated by arrow F. The gas being warmer than wafer 13, stream F provides a local zone 19 of supersaturation above a portion of surface 14. Preferably, the velocity of stream F is colinear and equal to the velocity of wafer motion, indicated by arrow B, so that no turbulence results. The level of supersaturation is controllable and can be varied by varying the temperature of liquid 58 in bubbler jar 56, higher temperatures resulting in greater supersaturation levels. The temperature of tube 55 should also be controlled so as to avoid condensation.

With reference to FIG. 5, another alternate embodiment of the invention has, like the first and second embodiments in FIGS. 1-3, a support 11 for a test object 13 having a surface 14 with particles 15. The test object 13 moves in a direction B so that droplets 21 condense on particles 15 on a portion of surface 14 as it moves through a local zone 19 of vapor supersaturation toward a scan path of a scanning laser beam 25. Beam 25 scans in a direction approximately perpendicular to direction B and light 33 scattering from droplets 21 are reflected by a collector 31 to a detector 47 positioned to receive the light 33. However, in this alternative embodiment, a plurality of wicks 60-63, here four in number, are disposed closely spaced above the surface 14. Each wick 60-63 is, in a manner similar to wick 17 in the first two embodiments, in fluid communication with one of a plurality of sources of vaporizable liquid material and is preferably heatable, as by means of an electric current flowing through conductive wicks. Each of the sources of vaporizable liquid material has a different composition, and only one of the materials is selected at one time for vaporization by its corresponding wick 60-63. For example, in FIG. 5, heating current through wick 62 has been turned on to vaporize and produce a zone of supersaturation of the volatile material drawn by wick 62. The other wicks 60-61 and 63 are unheated. The nonselected wicks 60-61, and 62 might also be removed from its source of material or otherwise prevented, such as by pinching, from drawing vaporizable liquid.

With reference to FIG. 6, in yet another embodiment, a test object 13 with a surface 14 to be tested for particles 15 is moved in a direction B on a support 11. A plurality of wicks 60-63, here four in number, are disposed closely spaced above surface 14, and are, like wick 17 in FIG. 1A, each in fluid communication with one of a plurality of sources of vaporizable liquid material. As in FIG. 5, each source has a different composition and only one of the liquid materials is ordinarily selected at any one time for vaporization by its corresponding wick 60 or 63. The embodiment also includes a source 53 of a carrier gas communicating with a manifold 57 via a tube 55. Like the embodiment in FIG. 3, the carrier gas may be any inert gas capable of holding vapor from a wick 60-63. Manifold 57 surrounds the plurality of wicks 60-63 on top and sides so that the stream of carrier gas containing a selected vaporized material is directed toward the surface. In this manner, a zone of supersaturation is provided locally on surface 14 immediately below manifold 57, and as a result droplets 21 of the selected liquid material from one of the wicks condense on a class of particles 15 on a portion of the surface 15 as it moves beneath manifold 57. A beam 25 scans in a direction approximately perpendicular to direction B and light 33 scattered from the droplets 21 are reflected by a collector 31 to a detector 47 positioned to receive the light 33.

With reference to FIG. 7, still another embodiment includes a plurality of bubbler jars 66A-D like bubbler jar 56 in FIG. 4. The apparatus is the same as in FIG. 4 except for the connections between gas supply 53 and tubing 55. In this multiple bubbler arrangement, tube 54 from gas supply 53 splits into a plurality of feeder tubes 59A-D, here four in number. Each feeder tube 59A-D communicates with one of the bubbler jars 66A-D through valves 64A-D on tubes 59A-D. Each bubbler jar 66A-D has a different composition of vaporizable liquid material, and only one of the materials is ordinarily selected by valves 64A-D at any one time. The gas bubbles through one of the jars 66A-D and exits through a corresponding exit tube 70A-D. Each exit tube 70A-D preferably has a valve 68A-D which opens and closes in synchronization with corresponding feeder tube valves 64A-D. The exit tubes 70A-D connect to tube 55 which then terminates above a wafer surface 13, as in FIG. 4.

By using several different vaporizable fluid sources it is possible to learn something about the nature of the particles that are detected and to classify them according to their chemical nature. For example, particles which wet or dissolve in certain fluids act as much better precipitation centers for these fluid vapors than vapors of fluids which do not have these characteristics. Thus, polar solvent vapors will tend to condense on ionic salt particles and are less likely to condense on nonionic material particles. Similarly, nonpolar solvent vapors will condense less easily on ionic salts than on nonionic material. By running several wicks 60-63 over the wafer 13 and activating a selected one at a time, it is possible to produce condensation on selected particles. By looking at the condensation patterns for various vapors in different scans it becomes possible to classify the particles on the surface 14 by chemical type.

Accordingly, a method of the present invention comprises providing a first supersaturated vapor composed of material of a first chemical characteristic over a test surface, whereby droplets condense on a first set of particles on the surface and scanning the surface so as to detect the droplets. These steps are repeated a predetermined number of times, in FIG. 5, 6 or 7 there would be up to four scans, with other supersaturated vapors composed of materials of other chemical characteristics, whereby droplets will condense on other sets of particles on the surface and will be subsequently detected. The detections from the several scans are compared and the particles are classified according to the vapor material or materials for which they act as precipitation centers. For example, photoresist residues might be identified by using the vapor of a resist solvent and particles around which droplets of such solvent condense would be classified as such residue.

With reference to FIG. 8, an alternative embodiment has a rotatable support 71 for holding a circular test object 73, such as a wafer, with a surface 74 to be tested. The support 71 rotates in a direction C and also translates on a spindle 75 in a direction D. A wick 77 is in fluid communication with a source of vaporizable liquid material 80. An impermeable sheath 78 may cover the portion of the wick 77 not inside source 80 or over the desired zone 79 of supersaturation. Both the wick 77 and the laser beam 85 are stationary, while the surface 74 is rotated and translated under the beam 85 by support 71. The combined motion traces out a spiral path on the wafer covering the entire wafer surface 74. Because the beam 75 and wick 77 can be held stationary to one another, the physical condensation region 79 can be very small. Uniformity is thus better ensured than longer zones. However, a drawback is that scanning requires a longer period of time.

The present invention uses a heated wick or bubbler to provide a local zone of controlled vapor supersaturation and a laser scanner to detect very small particles on a surface. Because supersaturation levels can be controlled and varied in known ways, size ranges of detected particles can be obtained in multiple scans. Other particle classification schemes use different vapor compositions to determine a particle's chemical nature. While this invention is particularly useful on unpatterned wafers, it can also be combined with other techniques known in the art to detect and classify particles in patterned wafers.

We claim:

1. A particle detection apparatus comprising,
   means for supporting an object, a surface of which can be tested,
   means for providing a local zone of vapor supersaturation over a portion of said surface, whereby droplets of liquid can condense around any particles on said object in said portion of said surface,
   means for directing a light beam adjacent to said local zone of vapor supersaturation toward said surface,
   means for providing relative movement of said object with respect to said local zone of vapor supersaturation and said adjacent light beam so as to cause relative movement of said portion of said surface having said droplets into a path of said beam, whereby light from said beam is scattered by said droplets, and
   means positioned in scattered light receiving relation to said surface for detecting light scattered by said droplets, whereby particles on said object around which said droplets have condensed are detected.

2. The particle detection apparatus of claim 1 wherein said means for providing a local zone of vapor supersaturation comprises a source of vaporizable liquid material, a wick in fluid communication with said liquid source and disposed over said portion of said surface, and
   means for heating said wick so as to vaporize liquid material drawn from said liquid source by said wick.

3. The particle detection apparatus of claim 2 wherein said means for providing a local zone of vapor supersaturation further comprises a source of a carrier gas and means in fluid communication with said carrier gas source and with said heated wick for directing a vapor stream toward said portion of said surface, said vapor stream being composed of vaporized liquid material in said carrier gas.

4. The particle detection apparatus of claim 3 wherein said vapor stream has zero velocity relative to said surface.

5. The particle detection apparatus of claim 1 wherein said means for providing a local zone of supersaturation comprises a source of carrier gas, a bubbler jar having a vaporizable liquid material, means for bubbling said carrier gas through said jar of vaporizable liquid material, and means in communication with said jar and terminating above said surface for directing a vapor stream, composed of vaporized liquid material in said carrrier gas, toward said portion of said surface.

6. The particle detection apparatus of claim 1 wherein said light beam is a laser beam.

7. The particle detection apparatus of claim 1 wherein said means for supporting an object includes means for cooling said object below a temperature in which said droplets of liquid condense.

8. The particle detection apparatus of claim 1 wherein said means for providing a local zone of supersaturation comprises a plurality of sources of vaporizable liquid material of different compositions and means for selecting one of said sources.

9. The particle detection apparatus of claim 8 wherein said means for providing a local zone of supersaturation further comprises a source of carrier gas and a manifold in fluid communication with said carrier gas source, and said means for selecting one of said plurality of vaporizable liquid material sources comprises a plurality of selectably heatable wicks in fluid communication with said liquid material, said manifold partially surrounding said plurality of wicks so as to direct a vapor stream composed of a selected vaporized liquid material and said carrier gas toward said surface.

10. The particle detection apparatus of claim 8 wherein said means for providing a local zone of supersaturation further comprises a source of carrier gas, a plurality of bubbler jars, each jar having a different vaporizable liquid material, means for selectively bubbling said carrier gas through one of said jars of vaporizable liquid material, and a tube in selective communication with said one of said jars and terminating above said surface so as to direct a vapor stream composed of a selected vaporized liquid material and said carrier gas toward said surface.

11. A particle detection apparatus comprising,
    means for supporting an object with a surface to be tested,
    a source of vaporizable liquid material,
    a wick in fluid communication with said source and disposed over a portion of said surface, said wick being heatable so as to cause liquid material drawn by said wick to vaporize,
    means for heating said wick, whereby a local zone of vapor supersaturation is provided over said portion of said surface, droplets of liquid being thereby capable of condensing on any particles in said portion,
    a light beam source for producing a beam,
    means in a path of said beam for directing said beam in a scanning motion toward said surface, said beam scanning a path adjacent to said local zone of vapor supersaturation,
    means associated with said support for moving said object relative to said wick and said scanning beam path, whereby any droplets which condense are moved into said beam path so as to scatter said light beam,
    a light detector positioned to receive light scattered by any said droplets, whereby particles around which said droplets have condensed are detected.

12. The apparatus of claim 11 wherein said means for heating a wick comprises means for providing an electric current through said wick.

13. The apparatus of claim 11 wherein said light beam source is a laser.

14. The apparatus of claim 11 further comprising,
a source of a carrier gas, and
a manifold partially surrounding said wick and in fluid communication with said gas source so as to provide a gas stream around said wick directed toward said surface.

15. The apparatus of claim 11 further comprising,
additional sources of vaporizable liquid material, each material having a different composition, and
additional wicks, each wick capable of being in fluid communication with one of said additional sources, and disposed over said surface, each wick being selectably heatable.

16. The apparatus of claim 15 further comprising,
a source of carrier gas, and
a manifold partially surrounding said wick and said additional wicks in fluid communication with said gas source so as to provide a gas stream around said wicks directed toward said surface.

17. The apparatus of claim 11 wherein said means for moving said object moves said object in a first direction and said means for directing said beam produces a beam path in a second direction substantially perpendicular to said first direction.

18. A method of detecting and classifying particles on a surface comprising,
(a) providing a first supersaturated vapor over a test surface, whereby droplets condense on a first set of particles on said surface,
(b) scanning said surface so as to detect said droplets,
(c) repeating steps (a) and (b) a predetermined number of times with other supersaturated vapors, whereby droplets condense on other sets of particles on said surface and are subsequently detected, and
(d) comparing said droplet detections from the repeated scans and classifying said particles on said surface according to the scan or scans in which their corresponding droplets are detected.

19. The method of claim 18 wherein said first supersaturated vapor is supersaturated to a first level, droplets condensing on particles of at least a first minimum size, and said other supersaturated vapors are supersaturated at other levels, droplets condensing on particles of at least other minimum sizes, said particles being classified into a plurality of relative size ranges corresponding to the supersaturation levels needed for their droplet detection.

20. The method of claim 18 wherein said first supersaturated vapor is composed of material of a first chemical characteristic, other supersaturated vapors being composed of materials of other chemical characteristics, said particles being classified according to the vapor material or materials for which they act as precipitation centers.

21. The method of claim 20 wherein said first supersaturated vapor is composed of a polar material, droplets of said material tending to condense on ionic salt particles on said surface, a second supersaturated vapor being composed of a non-polar material, droplets of said nonpolar material tending to condense on particles of nonionic material.

22. The method of claim 20 wherein one of said supersaturated vapors is composed of a photoresist solvent, particles around which droplets of said solvent condense being classified as photoresist residue.

23. The method of claim 18 wherein comparing said droplets includes counting the number of droplets detected in each scan and obtaining the number of particles in each class.

24. The method of claim 18 wherein comparing said droplets includes locating the position of detected droplets in each scan and matching any common positions in the plurality of scans, droplets detected in different scans which are determined to have matching common positions being designated as corresponding to a single particle.

25. The method of claim 18 wherein scanning said surface comprises,
directing a beam toward said surface, said beam being adjacent to a local zone of vapor supersaturation over said surface,
providing relative movement of said surface with respect to said beam and said local zone so as to cause relative movement of a local surface portion having said droplets into a path of said beam, said beam being scattered by any such droplets, and
detecting and measuring said scattered beam.

26. The method of claim 25 wherein a laser beam is directed toward said surface.

27. The method of claim 18 wherein providing a supersaturated vapor comprises,
providing a source of vaporizable liquid material,
disposing a wick in fluid communication with said liquid source over a local portion of said surface, the wick drawing said liquid material from said source, and
heating said wick so as to vaporize said liquid material drawn by said wick.

28. The method of claim 27 wherein providing a supersaturated vapor further comprises,
directing a stream of carrier gas for said vaporized liquid material around said wick toward said surface.

29. The method of claim 28 wherein said stream is directed so as to have zero velocity relative to said surface.

30. The method of claim 18 wherein providing a supersaturated vapor comprises,
providing a source of vaporizable liquid material,
bubbling a carrier gas through said liquid material, whereby said gas becomes saturated with said liquid material, and
directing a stream of said vapor saturated carrier gas toward said surface, said gas being warmer than said surface.

* * * * *